United States Patent [19]

Nunogaki

[11] 4,178,152
[45] Dec. 11, 1979

[54] CELL FRAGILITY TESTING METHOD AND APPLIANCE THEREFOR

[75] Inventor: Yoshiaki Nunogaki, Nagaokakyo, Japan

[73] Assignee: Sanki Engineering Ltd., Japan

[21] Appl. No.: 880,159

[22] Filed: Feb. 22, 1978

[30] Foreign Application Priority Data

Feb. 24, 1977 [JP] Japan .................................. 52-19611
Feb. 24, 1977 [JP] Japan .................................. 52-19612
Feb. 24, 1977 [JP] Japan .................................. 52-19613

[51] Int. Cl.² .......................................... G01N 33/16
[52] U.S. Cl. .................................... 23/230 B; 233/25; 422/72; 424/12
[58] Field of Search ............... 23/230 B, 253 R; 128/2 G; 233/25; 424/11, 12; 422/72

[56] References Cited

PUBLICATIONS

K. Takagi et al., Clinical Blood, 17(11), 1153–1160 (1976).
K. Kitazima et al., J. Lab. Clin. Med., 85(5), 855–865 (1975).
S. Ogita et al., J. Jap. Soc. Obstetrics & Gynecology, 27(10), 1099–1102 (1975).
Y. Ito et al., Nature, 212(5066), 985–987 (Dec. 3, 1966).
"Clinical Diagnosis", I. Davidson et al., eds., 14th Edition, 149–155, W. B. Saunders Co., Phila., 1969.

*Primary Examiner*—Sidney Marantz
*Attorney, Agent, or Firm*—Wenderoth, Lind & Ponack

[57] ABSTRACT

A method of and an appliance for use in testing the osmotic fragility of blood cells by the use of the CPC method involving a coil column containing an aqueous solution of a salt mixed with one or both of a viscosity modifier and a hemolysis promotor. This coil column, after the blood to be tested has been injected, is centrifuged while undergoing a planetary motion to cause the blood cells to undergo hemolysis. After this hemolysis, a hematological pattern is developed in the coil column, the position of the coil column at which such hematological pattern has been developed being indicative of the osmotic fragility of the subject blood.

5 Claims, 10 Drawing Figures

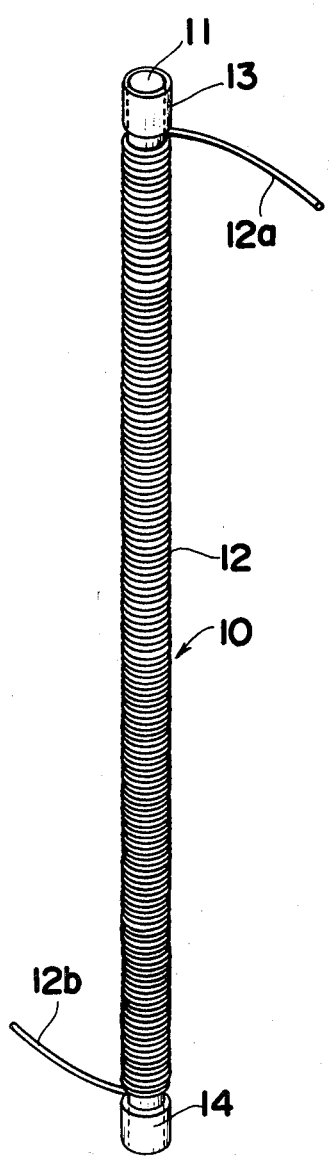
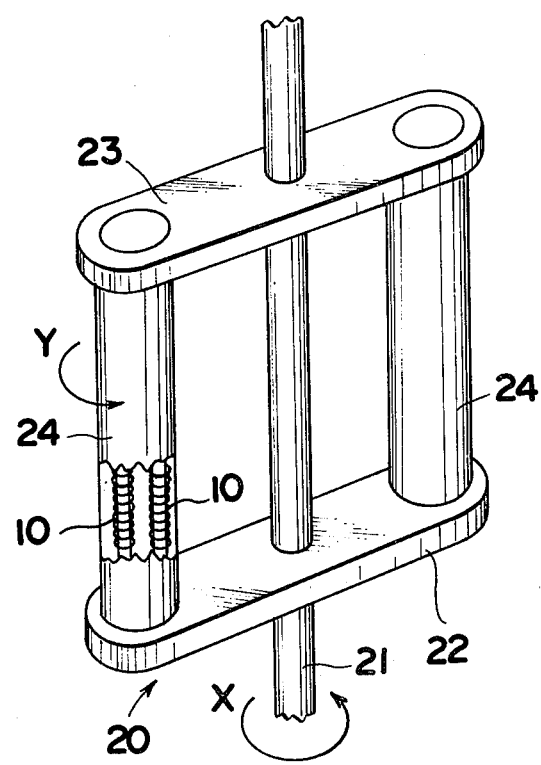
Fig. 1
Fig. 2

CELL FRAGILITY TESTING METHOD AND APPLIANCE THEREFOR

The present invention relates to the testing of the osmotic fragility of blood cells and, more particularly, to a method of and an appliance for use in determination of the osmotic fragility of blood cells.

As is well known to those skilled in the art, particularly, in the medical field, analysis of the blood of, for example, a human being often reveals not only the race, the type of blood, the composition of blood and the age of such human being, but also the presence of disturbances of the normal hematologic pattern of such blood which are often associated with disease. Biological determination of these particulars primarily relies on the hematologic pattern developed by the blood constituents, which is closely associated with the osmotic fragility of blood generally expressed in terms of an osmotic pressure at which hemolysis, that is, destruction of red cells in the blood, takes place.

Among many other methods, Parpart's method and Dannon's method are well known to those skilled in the art as a method for the determination of the cell osmotic fragility (As for Dannon's method, see, "A Rapid Micromethod For Recording Red Cell Osmotic Fragility By Continuous Decrease Of Salt Concentration", Journal of Clinic Pathology, 16:377-382, 1963.)

According to Parpart's method, the osmotic fragility is carried out by the use of a plurality of vessels containing equal amounts of physiological salt solution of different salt concentration, into which equal amounts of blood to be tested are injected. This is obviously time-consuming and complicated procedure because of the employment of a plurality of vessels with a relatively large amount of blood required.

On the other hand, Dannon's method requires the employment of a single vessel containing a physiological salt solution, the concentration of salt in the solution being subsequently increased after a predetermined amount of blood to be tested has been injected. Addition of the salt into the solution within the vessel to increase the salt concentration, which is effected after the predetermined amount of blood to be tested has been injected, is interrupted when and after hemolysis has taken place. Dannon's method is more convenient than Parpart's method, however, it is complicated and time-consuming in that it requires addition of salt to the solution a number of times to increase the salt concentration.

Both Parpart's and Dannon's method have a common disadvantage in that analysis of the blood to be tested can not complete in a relatively short period of time because of the complicated testing procedure described above.

As an improved version of cell fragility testing method developed for substantially eliminating the above described disadvantages and inconveniences, there is well known a coil planet centrifugal method. This improved method employs a coil planet centrifuge and is generally referred to as CPC method. The principle and applicability of the CPC method in the medical field are well known to those skilled in the art as disclosed in, "Nature", Vol. 212, No. 5066, pages 985 to 987, Dec. 3, 1966.

In general, the CPC method employs a testing coil column composed of a predetermined length of tube helically wound around an elongated support rod, into which tube a physiological salt solution is filled preparatory to injection of a predetermined amount, for example, 5 to 10μ liter, of blood to be tested. Usually, the salt solution in the coil column, that is, within the helically wound tube, has a concentration gradient, continuously varying from one end to the other end of the coil column so far as the cell fragility test is involved.

The coil column, after the blood to be tested has been injected into the helically wound tube from one end thereof where the saline concentration is isotonic and the opposed ends thereof have been closed, is placed on a centrifuge operable not only to apply a centrifugal force to the coil column in a direction perpendicular to the longitudinal axis of the coil column, but also to cause the coil column to undergo a planetary motion. As the centrifuge is operated this way, the blood cells helically move from the isotonic concentration area of the solution towards the hypertonic concentration area of the same solution within the helically wound tube, the consequence of which is a development of a hematological pattern of the blood at a position of the coil column where hemolysis has taken place. Since the position of the column where the hemolysis of a particular type of blood takes place varies, for example, depending upon the presence or absence of, and/or the type of, a disease in the human being whose blood has been tested, diagnosis of the the physical condition of such human being can readily be facilitated. This is possible because, as is well known to those skilled in the art, the erythrocytes respond to change in osmotic pressure of the extracellular fluid by swelling in hypotonic fluids and by shrinking in hypertonic fluids, the higher the osmotic pressure, the more readily the cells tending to rupture.

Examples of the applicability of the CPC method in diagnosing hematologic disorders, liver diseases, bile diseases and gastrointestinal diseases and in predication of the potential hemolytic abnormalities in infants, are disclosed in the medical literature, such as "Clinical Blood" Vol. 17, No. 11 (1976), "Journal of Laboratory and Clinical Medicine" Vol. 85 (1975) and "Journal of Japanese Society of Obsterics and Gynecology" Vol. 27, No. 10 (1975).

However, according to the conventional CPC method described above, the coil column has to be prepared shortly before the actual testing is carried out, and the coil column, once the saline solution is placed in the helically wound tube, cannot be stored for a prolonged period of time, or otherwise the concentration gradient of salt in the solution will be destroyed as the time passes. This means that an analyst performing the blood test is required to have, in addition to a knowledge of medicine necessary to diagnose diseases, the skill necessary to prepare the coil column having a continuous saline concentration gradient and that, even though the coil column having a continuous saline concentration gradient has successfully been prepared, saline particles in the solution tend to be diffused, when subjected to the centrifugal force, with the concentration gradient consequently deviating from its optimum condition. In particular, the diffusion of the saline particles in the solution to such an extent that the optimum concentration gradient is deviated adversely affects an accurate and precise determination of the osmotic fragility of blood cells which in turn adversely affects the hematologic pattern of such blood cells.

Accordingly, the present invention has been developed with a view towards substantially eliminating the above described disadvantages and inconveniences inherent in the conventional CPC method and is intended to provide a coil column having an improved saline solution of a nature capable of maintaining a concentration gradient for a substantially prolonged period of time.

Another important object of the present invention is to provide a coil column of the type referred to above, which substantially precludes the necessity of preparation of the coil column shortly before the actual testing is carried out and which can be placed on the market.

A further important object of the present invention is to provide a coil column of the type referred to above, which substantially minimizes the burden of an analyst or a physician who has heretofore been required to have the skill necessary to prepare the coil column.

It is a related object of the present invention to provide a method for testing the osmotic fragility of blood cells by the use of the coil column of the type referred to above.

These and other objects and features of the present invention will become apparent from the following description taken in conjunction with a preferred embodiment thereof with reference to the accompanying drawings, in which:

FIG. 1 is a perspective view of a testing coil column employed in the present invention;

FIG. 2 is a schematic perspective view of a centrifuge, showing the details of how the coil columns are mounted on the centrifuge;

Figure 4:
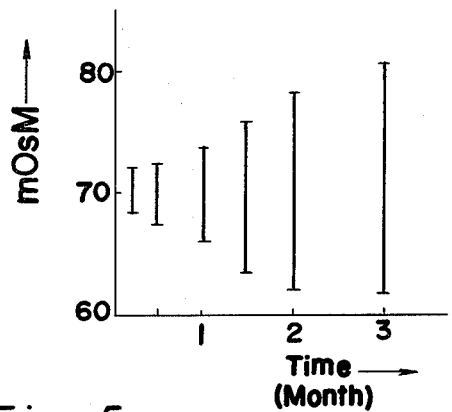
Figure 5:
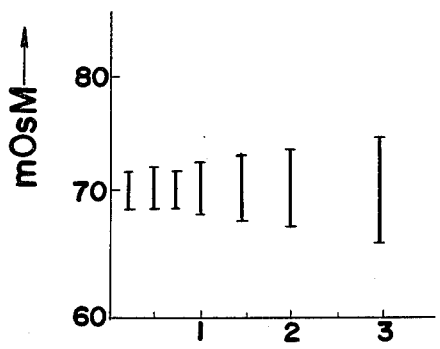
Figure 6:
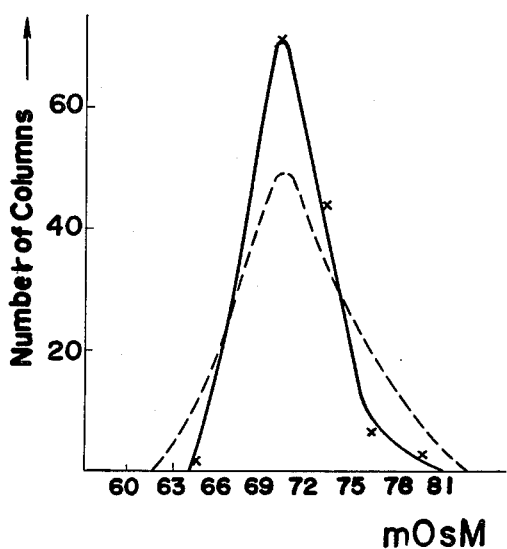

FIGS. 3(b) to 3(e) are diagrams showing respective hematologic patterns of the rat blood of different aging, employed for the purpose of illustrating the applicability of a CPC method in determination of the age of a blood;

FIG. 4 is a graph illustrating the shelf life characteristics of conventional coil columns;

FIG. 5 is a graph similar to FIG. 4, showing the shelf life characteristics of the coil columns according to the present invention; and FIG. 6 is a graph illustrating the difference in performance between the prior art coil column and the coil column according to the present invention.

Before the description of the present invention proceeds, it is to be noted that like parts are designated by like reference numerals throughout the accompanying drawings.

Referring first to FIGS. 1 and 2, structural features of equipments employed in the conventional CPC method will now be described for the purpose of facilitating a better understanding of the present invention.

The CPC method employs a coil column, generally designated by 10 and best shown in FIG. 1, and a centrifuge generally indicated by 20 and schematically shown in FIG. 2. The coil column 10 comprises an elongated support rod 11, either hollow or rigid and made of any suitable material, preferably a transparent synthetic resin. An elongated flexible tube 12, made of any suitable synthetic resin of a nature inactive to the blood to be tested and also to a solution of a particular composition contained therein as will be described later, preferably, polyethylene or polyvinyl chloride, is wound in a number of turns on the support rod 11 and has its opposed end portions 12a and 12b retained in position by associated end portions of the support rod 11. In order to retain the end portions 12a and 12b of the tube 12 in the manner described above, each end of the support rod 11 has a split groove or a retaining hole (not shown) which radially extends completely through the diameter of the support rod 11 and through which the associated end portion 12a or 12b of the tube 12 is passed.

The coil column 10 further comprises a pair of retainers 13 and 14 respectively removably mounted on the end portions of the support rod 11. The retainers 13 and 14 may be in the form of either elastic band-shaped rings or caps having an inner diameter substantially equal to or slightly smaller than the diameter of the support rod 11, the function of which will be described later.

The centrifuge 20 is shown to comprise a shaft 21 having a substantially elongated gear box 22 mounted thereon for rotation together with said shaft 21. The shaft 21 also has a substantially elongated plate 23 mounted for rotation together with said shaft 21 and also for axial movement in a direction parallel to the longitudinal axis of the shaft 21 close towards and away from the gear box 22. Positioned between the gear box 22 and the plate 23 is a pair of holders 24 of the same construction each having a plurality of elongated chambers arranged in a circular row about the longitudinal axis of said holder 24. Each of the holders 24 has one end having a gear (not shown) rigidly mounted thereon and held in engagement with one of gears of a train (not shown) housed within the gear box 22 so that, during the rotation of the shaft 21 driven by a motor (not shown) in a direction indicated by the arrow X, the holders 24 rotate about the longitudinal axis of the shaft 21 on one hand and rotate about their own longitudinal axes in a direction as shown by the arrow Y. The chambers in each of the holders 24 are adapted to accommodate therein a corresponding number of coil columns during the actual test. Each of the holders 24 is removable from the centrifuge 20 in any suitable manner, for example, by upwardly shifting the plate 23. However, since the centrifuge 20 is well known to those skilled in the art and since the present invention is not directed to the centrifuge itself, the details thereof are herein omitted.

In any event, from the foregoing, it is clear that during operation of the centrifuge, i.e., rotation of the shaft 21, not only a centrifugal force is applied to the coil column 10, but also the latter undergoes a planetary motion.

Referring back to FIG. 1, so far as the CPC method is involved, the tube 12 is preferably of a type having an inner diameter within the range of 0.3 to 1.5 mm., more preferably, about 0.5 mm. and a length of about 3 m. In combination therewith, the support rod 11 is preferably of a type having an outer diameter within the range of 5 to 20 mm. In any event, any tube can be employed so far as the inner diameter is sufficient to allow the blood cells of interest to move within the hollow of the tube 12.

The number of turns of the tube around the support rod 11 may be suitably selected, but about 150 turns is preferred and, so far as the 150 turns is involved, the employment of the support rod, having a length of about 20 cm. and an outer diameter of about 5 mm., in combination with the tube having an outer diameter of about 1.1 mm. and a length of about 3 m. appears to be recommendable.

In accordance with the present invention, the coil column 10 contains therein a saline solution filled in the tube 12 so as to have a concentration gradient over the substantially entire length of the tube 12, the composition of which solution will now be described.

The saline solution contained in the coil column 12 is an aqueous solution of one of salts, such as NaCl, NaI, NaBr, KI, KCl and KBr, mixed with one or a mixture of a viscosity modifier and a hemolysis promotor.

The viscosity modifier employed in the present invention includes monosaccharides, such as glucose and fructose, oligosaccharides, such as sucrose, water-soluble, neutral polysaccharides, such as starch, dextran, glycogen, mannan and purullan, electrolytic polysaccharides, such as acacia, alginic acid and pectin, water-soluble proteins, such as gelatine and albumin, synthetic or semi-synthetic, water-soluble polymers, such as polyethylene glycol, polypropylene glycol, polyvinyl pyrrolidone, methyl cellulose, ethyl cellulose, polyvinyl alcohol, hydroxymethyl cellulose and carboxymethyl cellulose, and glycerol. Preferably, the employment of any one of dextran and polyethylene glycol is recommended as a viscosity modifier.

The amount of the viscosity modifier to be mixed with the saline solution irrespective of the hemolysis promotor as will be described later varies depending upon the inner diameter of the tube 12 of the coil column 10 and, however, is preferably so selected that, in the case where the tube 12 is of a type having a length of 3 m. and an inner diameter of 0.5 mm., the saline solution within the hollow of the tube 12 as a whole attains a viscosity within the range of 1.05 to 200 c.p.s. at 20° C., preferably within the range of 1.05 to 50 c.p.s. at 20° C. and more preferably within the range of 0.5 to 2.0 c.p.s. at 20° C. irrespective of the concentration gradient of the saline solution.

In particular, where the tube is of a type having a length of 3 m. and an inner diameter of 0.5 mm. and filled with an aqueous solution of NaCl, the amount of the viscosity modifier be preferably so selected as to render the solution to have a viscosity within the range of 1.05 to 2.0 c.p.s. at 20° C.

Examples of hemolysis promotor which may be employed in the present invention are surface active agents, such as lysolecithin, bile acid and dodecyl sodium sulfate; saponine; alkaloids; extracts of snake venom and bee venom; vegetable hemolysins, such as ricin, abrine and crotin; bacterial hemolysins, such as staphylolysin, streptolysin and vibriolysin; acids; alkalis; cyclic peptide type antibiotic substances, such as valinomycin, enniatin and actinomycin; crown ethers; protein cross linking agents, such as glutaraldehyde and dialydehyde starch; heavy metal ions, such as mercury, lead and cadmium, of a kind capable of non-reversibly bonding to protein; enzymes inactivators or protein modifiers, such as P-mercury benzoate, N-ethylmaleimide and ididopropylphosphoridate; oxidizing agents, such as hydrogen peroxide, sodium perchlorate and benzoyl peroxide; reducing agents, such as ascorbic acid, methylene blue, hydroquinone, 6-hydroxide pamine, dithiotoleithol and mercaptoethyl alcohol; and oxido-reductases, such as peroxidase, lipoid dehydrogenase and glutathione reductase.

In preparation of the saline solution according to the present invention, one or more of these hemolysis promotors may be employed with or without the viscosity modifier. Where one or more of these hemolysis promotors are to be mixed with the saline solution containing one of the salts with or without the viscosity modifier, an aqueous solvent, such as methanol, ethanol, ethylene glycol, cellosolve, glycerol, polyalkylene glycol oil, dimethyl formamide, dimethyl sulfoxide or trimethyl phosphate, may be employed.

A method of filling the saline solution of a particular composition according to the present invention into the helically wound tube 12 in such a manner that the concentration of the saline solution continuously varies from one of the opposed end positions of the tube 12 towards the other of said opposed end portions of the tube 12 may be carried out in any known manner, but may preferably be carried out by the use of an injecting device disclosed in the Japanese Patent Laid-Open Publication No. 79393/1976.

The concentration gradient of the saline solution in the coil column according to the present invention varies depending upon the purpose for which the blood testing is made, but may be such that the concentration continuously varies from 30 to 280 mOsM, preferably, from 30 to 150 mOsM.

The saline solution of the above described composition may contain a pH controller and/or a buffer agent.

Referring now back to FIGS. 1 and 2, after the saline solution of the composition as hereinbefore described has been injected into the tube 12 either before or after the helically winding of the tube 12 around the support rod 11, the opposed ends of the tube 12 are tightly closed in any suitable manner, for example, by heat-press to clog the opposed ends of the tube 12.

After the saline solution has been filled in the tube 12 and after the latter has been helically wound on the support rod 11 with the closed end portions 12a and 12b passed, for example, through the respective holes, the retainers, for example, the elastic caps 13 and 14, are mounted on the respective end portions of the support rod 11 in readiness for sale in the market.

An analyst or a physician, when it has purchased the coil column according to the present invention, should cut one of the closed end portions 12a and 12b of the helically wound tube 12 so that a droplet of blood to be tested can be injected into the saline solution within the tube 12. Depending upon the purpose for which the blood cells are to be tested, injection of the blood droplet may be made either into one of the opposed ends of the tube 12, where there is a hypotonic or isotonic solution, or into the other of the opposed ends of the same tube 12 where there is a hypertonic solution.

After the droplet of blood has been injected in the matter as hereinbefore described, the end portion of the tube 12 through which the blood has been injected into the tube 12 is again closed. This closing may be done by further axially inserting the adjacent cap 13 or 14 until a portion of the tube 12 which extends through the corresponding hole in the support rod 11 is clamped by the cap 13 or 14 in cooperation with the outer peripheral surface of that end portion of the support rod 11. A similar closing may be effected to the other end portion of the tube 12 to remove an unnecessary portion of the tube 12 which outwardly extends from the support rod 11.

Thereafter, the coil column 10 is placed on the centrifuge in the manner described with reference to FIG. 2. After the coil column has been revolved at a predetermined velocity about the longitudinal axis of the shaft 21 while simultaneously undergoing a planetary motion relative to the shaft 21 at a predetermined velocity for a predetermined period of time, for example, 10 minutes, the blood cells destruct, that is, undergo hemolysis, at a definite position of the coil column, developing a hematologic pattern thereat. From the foregoing, it is clear that, by reading the position of the coil column where the hematologic pattern of the blood tested has been developed, the osmotic fragility of the blood cells can be determined. For a given person, this osmotic fragility varies depending upon whether such person is in good health or whether such person suffers from illness and, therefore, by analyzing the developed hematologic pattern in any known manner by the use of any suitable medical measuring instrument, a particular disease the person actually suffers from can be diagnosed.

The improved shelf life of the coil column containing the saline solution according to the present invention will now be exhibited by way of examples.

EXAMPLE I

A plurality of coil columns each being 186 mm. in length and composed of a flexible transparent tube 12 having a length of 3,000 mm., an inner diameter of 0.5 mm. and an outer diameter of 1.1 mm., were prepared. The saline solution filled in the tubes of the respective coil columns was an aqueous solution of NaCl, the viscosity of which had been increased by the addition of dextran in an amount of 0.1% relative to the total weight of the solution.

All of the coil columns were stored at 4° C. and batches of coil columns, each consisting of 100 coil columns, were tested at different times under the same condition.

During the test, all of the coil columns of each batch were injected with 10$\mu$ liter of blood collected from a healthy human being and applied with a centrifugal force while undergoing a planetary motion under the following conditions.

Radius of Revolution: 117 mm.
Velocity of Revolution: 1,600 r.p.m.
Velocity of Planetary Motion: 16 r.p.m.

The test results are shown in FIG. 5.

For the purpose of comparison, the conventional coil columns, differing from the coil columns of the present invention in that they contained only an aqueous solution of NaCl, were tested in a similar manner as hereinabove described, the test results of which are shown in FIG. 4.

Comparing the graph of FIG. 5 with that of FIG. 4, it is clear that an average size of the hematologic pattern developed in the batch of the coil columns according to the present invention which had been stored for three months does not vary so much as that of the conventional coil columns which had been stored for the same period of time, as compared with an average size of the hematologic pattern developed in the coil columns which had been stored for about one week.

In summary, the presence of the viscosity modifier in the saline solution improves the shelf life of the coil column.

EXAMPLE II

A plurality of coil columns, similar to that described under Example I, were prepared and tested in the same manner as in Example I immediately after they had been prepared without being stored. For the purpose of comparison, an equal number of the conventional coil columns, similar to that employed under Example I, were also prepared and tested immediately after they had been prepared, in the same manner as in Example I. Variation in position at which the hemolysis had taken place was plotted as shown in the graph of FIG. 5 wherein a curve represented by the solid line illustrates variation in the coil columns according to the present invention while a curve represented by the broken line illustrates variation in the conventional coil columns.

Comparison of the curves shown in the graph of FIG. 6 illustrates that the number of the coil columns which had given a relatively large variation in position at which the hemolysis had taken place is smaller in the present invention than according to the prior art and that a more accurate and precise determination of the osmotic fragility of blood cells can be carried out with the coil columns of the present invention than with the conventional coil columns only because of the presence of the viscosity modifier, i.e., dextran, in the coil columns of the present invention.

The following example illustrates that the coil column according to the present invention can be used in determination of the age of red cells when used in the CPC method.

EXAMPLE III

A rabbit was treated with an intravenous injection so that $^{59}$Fe could be admitted into the vein, and the life cycle of erythrocytes of the rabbit blood was traced in the following manner.

The blood of the rabbit so treated was collected at different time subsequent to the intravenous injection according to Prankard's method and was subsequently centrifuged by the use of a conventional centrifuge operated at 700 to 1,000 r.p.m. so that the erythrocytes could be classified into upper, intermediate and lower layers according to the specific gravity thereof, the specific gravity of the erythrocytes gradually increasing in the order from the upper layer towards the lower layer. Measurement of the radioactivity emitted from $^{59}$Fe contained in each of the upper, intermediate and lower layers of the rabbit blood within a container revealed that the intensity of radioactivity was of the highest value in the upper layer of the blood two days after the injection, of the highest value in the intermediate layer of the same blood 14 to 21 days after the injection and of the highest value 35 days after the injection. The erythrocytes in the rabbit were formed in the bone marrow with Fe taken as a material and completed their life cycle about 50 days. The erythrocytes, which had completed their life cycle were metabolized in the spleen.

The foregoing test illustrates that some of the erythrocytes having the smallest specific gravity, that is, those in the upper layer of the blood, are younger than that having the greatest specific gravity, that is, those in the lower layer of the blood.

EXAMPLE IV

In the same manner as under Example III, the rabbit blood was classified into the upper, intermediate and lower layers within a container. Respective droplets of blood in the lower layer, a portion of the intermediate layer adjacent the lower layer, another portion of the intermediate layer adjacent the upper layer, and the upper layer were injected into the coil columns. These four coil columns were subsequently centrifugalized to give respective hematologic patterns of blood, the test results of which are shown in FIGS. 3(a) to 3(e).

It is to be noted that, in each of FIGS. 3(a) to 3(e), the coil column 10 is shown as horizontally laid with a hypertonic area of the solution positioned to the right of the drawing.

Figure 3A:
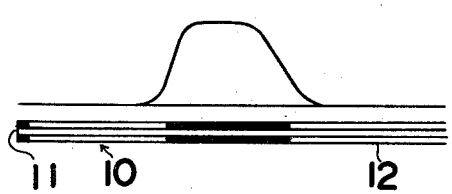
FIG. 3(a) is a diagram showing a hematologic pattern of a rat blood together with a spectrographic representation of such hematologic pattern.
Figure 3B:
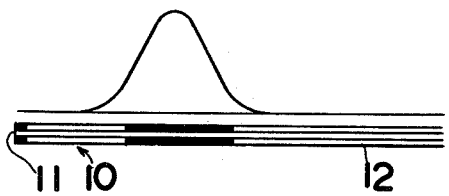
Figure 3C:
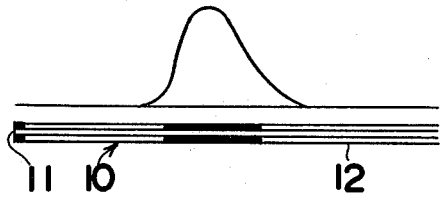
Figure 3D:
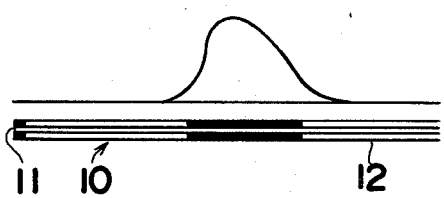
Figure 3E:
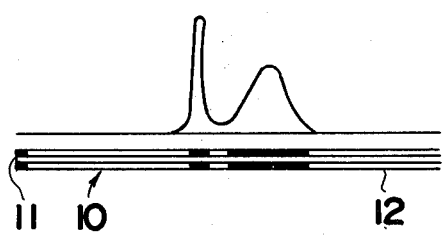

FIG. 3(a) illustrates a hematologic pattern of the rabbit blood without being classified.

FIG. 3(b) to 3(e) illustrate respective hematologic patterns of the rabbit blood in the lower layer, in the portion of the intermediate layer adjacent the lower layer, the portion of the intermediate layer adjacent the upper layer and the upper layer.

From the foregoing, it is clear that the young erythrocytes tend to undergo hemolysis in a higher concentration of the saline solution than the old erythrocytes. In other words, the osmotic fragility of the young erythrocytes is lower than that of the old erythrocytes or the osmotic resistance of the young erythrocytes is higher than that of the old erythrocytes.

The following examples are for the purpose of illustrating the applicability of the CPC method using the coil column of the present invention in diagnosing diseases.

EXAMPLE V 1 milliliter of blood was collected from each of 23 patients who were considered as having contracted liver functional disorders including acute and chronic hepatitis and liver cirrhosis. These lots of blood so collected were mixed with heparin as a anti-coagulant to avoid coagulation of the blood and subsequently injected into two groups of respective coil columns. Each of the coil columns of one group A had contained an aqueous solution of NaCl having a concentration gradient continuously varying from 30 to 150 mOsM while each of the coil columns of the other group B had contained an aqueous solution of ginseng saponine having a concentration gradient continuously varying from 0 to 40 $\mu$/ml. These coil columns of the groups A and B were centrifugalized according to the CPC method to develop the respective hematologic patterns.

A result of the test with the coil columns containing the aqueous solution of ginseng saponin has shown that the position of the coil columns at which hematolysis had taken place was shifted 12 to 40 mOsM towards the hypotonic area of the solution from the position (reading at 58 mOsM) of the coil column at which hematolysis of the blood collected from a healthy person had taken place in a saline solution of NaCl.

On the other hand, a result of the test with the coil columns containing the aqueous solution of NaCl has shown that the position of the coil columns at which hematolysis had taken place was shifted 5 to 15 mOsM towards the hypotonic area of the solution from the position (reading 58 mOsM) of the coil column at which hematolysis of the blood collected from the healthy person had taken place in the saline solution of NaCl.

From the foregoing, since the difference in osmotic fragility of blood between the healthy patient and the patients is greater with the aqueous solution of saponin than with the solution of NaCl, the presence of saponin is more effective in determination of the presence of the liver functional disorders.

EXAMPLE VI

Subsequent to 6 hospitalized patients contracting chronic hepatitis, the variation in hematologic pattern at different times was measured while, simultaneously therewith, any known testing of the function of the liver was performed. The coil columns used to develop the hematologic pattern described above had contained an aqueous solution of NaCl and ginseng saponine as under Example V.

During the hospitalization, values of serum enzymes such as GOT and GPT were between 200 tO 320 karmen units and, however, as the patients recovered, the GOT and GPT values decreased to 30 to 55 karmen units and 20 to 42 karmen units, respectively.

On the other hand, the position of the coil columns at which hematolysis had taken place read 45 to 15 mOsM shifted from the position (reading at 58 mOsM) at which hematolysis of the blood collected from a healthy person had taken place. It was three to seven days after the GOT and GPT values had reduced to the above described karmen units that the position of the coil columns at which hematolysis had taken place read a normal value of 58 mOsM.

Of the patients treated, three patients who had been discharged from the hospital and whose reading of the position at which hematolysis had taken place was far from the normal value through the GOT and GPT values had already been decreased were again hospitalized about one month subsequent to the discharge from the hospital. On the contrary thereto, the other patients, who had received a medical treatment until after the position at which hematolysis had taken place at a value comparable to the normal value with the GOT and GPT values decreased, have regained their health.

From the foregoing example, it is clear that the CPC methos is more effective in determining the abnormalities in function of the liver than the conventional biochemical testing method.

EXAMPLE VII

Lots of blood collected from 15 patients who had been considered as contracting anemias including iron deficiency anemia, aplastic anemia, anemia of malignancy and congenital hemolytic anemia, were tested according to the CPC method. The coil columns used contained an aqueous solution of NaCl, having a concentration gradient varying continuously from 150 to 30 mOsM, mixed with lysolecithin in an amount of 50 $\mu$m. Contrary to a normal value of 69 mOsM at which hemolysis of the blood of a healthy person had taken place, these patient's osmotic reading was within the range of 115 to 80 mOsM and therefore the osmotic fragility of the blood of these patients were higher than that of the healthy person.

From the foregoing, it is clear that the presence of the surface active agent, that is, lysolecithin, in the saline solution is effective in determining the presence of the anemia.

EXAMPLE VIII

Upon to blood collected from 23 patients who had been treated with an artificial kidney for a long period of time because of kidney failure, the CPC method was performed one or two times per week for four to six months to examine the hematologic pattern developed. The coil columns used contained an aqueous solution of NaCl, having a concentration gradient continuously varying from 150 to 30 mOsM, mixed with a reducing agent, such as methylene blue and hydroquinone in an amount of 20 to 50 $\mu$/ml.

During the treatment of the patients with the artificial kidney, biochemical test values of urea, creatinine, potassium and natrium did not vary. On the other hand, so far as the CPC method is involved, the patients could be classified into two groups X and Y. The group X consisted of 13 patients whose blood had shown no variation in hematologic pattern during the treatment while the group Y consisted of 10 patients whose blood had shown variation in hematologic pattern towards a hypertonic area of the solution in the coil columns during the same time. The patients of the group Y, even though treated with the artificial kidney, had subsequently shown reduction in weight, reduction in hematocrit value, development of a bodily edema and/or abnormal increase of reticulocytes, while the patients of the group X could have a normal social life while regularly treated with the artificial kidney.

From the foregoing, it is clear that the CPC method can be employed in determining the physical condition of a patient suffering from a kidney failure.

Although the present invention has been fully described by way of examples and with reference to the accompanying drawings, it is to be noted that various changes and modifications are apparent to those skilled in the art. By way of example, by analyzing the hematologic pattern developed by erythrocytes in the coil column of the present invention by use of a spectrograph or any other scanning optical recorder to give a particular characteristic curve of the hematologic pattern, disease diagnosis can be performed, including hematologic disorders, liver abnormalities, and bile abnormalities.

In addition, where the hematologic pattern developed by leucocytes and lymphoblasts in the coil column of the present invention is analyzed, the presence of leukemia, infection diseases, cancer and diffuse collagen disease can be determined. Where the hematologic pattern developed by blood platelets in the coil column of the present invention is analyzed, the presence of hirn-thrombose and purpura haemorrhagica thrombopenica can be determined.

Furthermore, by removing the tube, having a particular hematologic pattern of blood, from the support rod, then cutting a portion of the removed tube, where the hematologic pattern is present, into a plurality of fractions, and analyzing each of the fractions by any known assay method, the constituents of the blood can be determined, an example of which is illustrated in Table I.

retainers one for each end of the support rod for retaining the opposed ends of said tube at said corresponding end portions of the support rod; and an aqueous solution of a salt filled in the hollow of said tube and having a concentration gradient over the substantially entire length of said tube, said salt being selected from the group consisting of NaCl, NaBr, KCl, and KBr, and said solution being mixed with a viscosity modifier which is selected from the group consisting of monosaccharides, oligosaccharides, neutral polysaccharides, electrolytic polysaccharides, water-soluble proteins, synthetic water-soluble polymers, semisynthetic water-soluble polymers and glycerol.

2. A coil column as claimed in claim 1, wherein said solution is further mixed with a hemolysis promotor.

3. A coil column as claimed in claim 2, wherein said hemolysis promotor is selected from the group consisting of surface active agents, saponin, alkaloids, snake venom extracts, bee venom extracts, vegetable hemolysin, acids, alkaline materials, cyclic peptide type antibiotic substances, crown ether, protein cross linking agents, heavy metal ions of a type capable of non-reversibly bonding to proteins, enzyme inactivators, protein modifiers, oxidizing agents, reducing agents, and oxido-reductase.

4. A method of measuring the osmotic fragility of blood by the use of a coil column of a construction comprising an elongated tube helically wound on a support rod with its opposed ends retained in position at corresponding end portions of the support rod, and an aqueous solution of a salt filled in the hollow of the tube, said salt being selected from the group consisting of NaCl, NaBr, KCl and KBr, and said solution being mixed with at least one of a viscosity modifier and a hemolysis promotor, said viscosity modifier being selected from a group consisting of monosaccharides, oligosaccharides, neutral polysaccharides, electrolytic polysaccharides, water-soluble proteins, synthetic water-soluble polymers, semi-synthetic water-soluble polymers and glycerol, which comprises the steps of:

injecting a predetermined amount of blood to be analyzed into the hollow of the tube from one of the opposed ends of said tube;

closing said one of the opposed ends of said tube;

placing the tube in a centrifuge to apply a centrifugal force thereto while said coil column undergoes a planetary motion;

causing the blood cells to move in the solution within the tube during the continued centrifugation to Table I

| | Fraction Nos. (mOsM) | | | | |
|---|---|---|---|---|---|
| | I (<70) | II (70–85) | III (85–95) | IV (95-110) | V (>110) |
| Cholinesterase (uM/λ/hr/g.Hb) | 16.7 ± 1.0 | 13.6 ± 1.3 | 11.8 ± 1.0 | 11.9 ± 2.1 | 8.8 ± 0.8 |
| Glycose-6-phosphate dehydrogenase (miu/Hb/dl) | 434.1 ± 25.3 | 347.6 ± 66.5 | 310.2 ± 60.7 | 262.8 ± 60.6 | 166.8 ± 55.6 |
| Ca (mEq/g.Hb) | 14.6 ± 3.0 | 15.2 ± 5.8 | 17.2 ± 4.2 | 20.0 ± 5.1 | 22.6 ± 6.3 |
| Adenosine Triphosphate (mg/g.Hb) | 15.8 ± 2.2 | 15.2 ± 2.3 | 13.0 ± 2.7 | 12.0 ± 1.4 | 8.3 ± 0.6 |
| Total Fat | 54.7 ± 8.2 | 45.9 ± 8.9 | | | |
| 41.4 ± 8.8 (mg/g.Hb) | 36.7 ± 5.6 | 34.0 ± 5.0 | | | |
| Cholesterol | 40.6 ± 10.3 | 36.9 ± 8.3 | 31.2 ± 5.8 | 28.1 ± 7.2 | 24.5 ± 1.5 |

What is claimed is:

1. A coil column for use in a coil planet centrifuge for developing a hematologic pattern of blood, which comprises:

an elongated tube;

a support rod around which said elongated tube is helically wound, the opposed ends of said tube being retained in position at corresponding end portions of the support rod;

allow said blood cells to undergo hemolysis by the effect of an osmotic pressure differential; and causing the blood cells, which have undergone hemolysis, to develop a hematolgocial pattern in the helically wound tube.

5. A method as claimed in claim 4, wherein said hemolysis promotor is selected from the group consisting of surface active agents, saponin, alkaloids, snake venom extracts, bee venom extracts, vegetable hemolysin, acids, alkaline materials, cyclic peptide type antibiotic substances, crown ether, protein cross-linking agents, heavy metal ions of a type capable of non-reversing bonding to proteins, enzyme inactivators, protein modifiers, oxidizing agents, reducing agents and oxide-reductase.

* * * * *